US007047083B2

(12) United States Patent
Gunderson et al.

(10) Patent No.: US 7,047,083 B2
(45) Date of Patent: May 16, 2006

(54) METHOD AND APPARATUS FOR IDENTIFYING LEAD-RELATED CONDITIONS USING LEAD IMPEDANCE MEASUREMENTS

(75) Inventors: Bruce D. Gunderson, Plymouth, MN (US); Amisha S. Patel, Maple Grove, MN (US); Chad A. Bounds, St. Paul, MN (US); Edwin G. Duffin, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 484 days.

(21) Appl. No.: 10/260,676

(22) Filed: Sep. 30, 2002

(65) Prior Publication Data

US 2004/0064161 A1    Apr. 1, 2004

(51) Int. Cl.
*A61N 1/05* (2006.01)
(52) U.S. Cl. ...................... 607/116; 607/119
(58) Field of Classification Search ............. 607/9, 607/28, 30, 37, 115–138
See application file for complete search history.

(56) References Cited

U.S. PATENT DOCUMENTS

| | | | |
|---|---|---|---|
| 4,140,131 A | 2/1979 | Dutcher et al. | |
| 4,825,869 A | 5/1989 | Sasmor et al. | |
| 4,899,750 A | 2/1990 | Ekwall | |
| 4,944,746 A | 7/1990 | Iwata et al. | |
| 5,003,975 A | 4/1991 | Hafelfinger et al. | |
| 5,117,824 A | 6/1992 | Keimel et al. | |
| 5,137,021 A | 8/1992 | Wayne et al. | |
| 5,184,614 A | 2/1993 | Collins et al. | |
| 5,201,865 A * | 4/1993 | Kuehn | 607/8 |
| 5,215,081 A | 6/1993 | Ostroff | |
| 5,224,475 A | 7/1993 | Berg et al. | |
| 5,431,692 A | 7/1995 | Hansen et al. | |
| 5,507,746 A | 4/1996 | Lin | |
| 5,507,786 A | 4/1996 | Morgan et al. | |
| 5,534,018 A | 7/1996 | Wahlstrand et al. | |
| 5,549,646 A | 8/1996 | Katz et al. | |
| 5,660,183 A | 8/1997 | Chiang et al. | |
| 5,722,997 A | 3/1998 | Nedungadi et al. | |
| 5,741,311 A | 4/1998 | Mc Venes et al. | |
| 5,755,742 A * | 5/1998 | Schuelke et al. | 607/27 |
| 5,814,088 A | 9/1998 | Paul et al. | |
| 5,891,179 A | 4/1999 | Er et al. | |
| 5,897,577 A | 4/1999 | Cinbis et al. | |

(Continued)

FOREIGN PATENT DOCUMENTS

EP      0 715 866 A2 * 12/1996

(Continued)

*Primary Examiner*—Carl Layno
(74) *Attorney, Agent, or Firm*—Caroline F. Barry; Girma Wolde-Michael

(57) ABSTRACT

A method and apparatus for automatically detecting and diagnosing lead-related conditions is provided. Specifically, relatively short-term and relatively long-term impedance parameters are determined for detecting an impedance trend indicative of a lead-related condition such as an open circuit, which may be due to a conductor fracture or poor connection to an associated implantable medical device, or a short circuit due to an insulation breach. Monitoring of multiple lead impedance parameters is performed to diagnose a lead-related condition based on a number of diagnostic criteria. Supplementary analysis of multiple lead impedance parameter trends may be performed to identify lead-specific conditions, such as metal ion oxidation induced insulation degradation. A lead-related condition diagnosis and supporting data are stored in memory for uplinking to an external device for review by a clinician. A recommended corrective action and/or a patient notification signal for a lead-related condition may optionally be provided.

3 Claims, 9 Drawing Sheets

U.S. PATENT DOCUMENTS

| | | |
|---|---|---|
| 5,944,746 A | 8/1999 | Kroll |
| 6,067,473 A | 5/2000 | Greeninger et al. |
| 6,129,746 A | 10/2000 | Levine et al. |
| 6,141,585 A | 10/2000 | Prutchi et al. |
| 6,317,633 B1 | 11/2001 | Jorgenson et al. |
| 6,721,600 B1* | 4/2004 | Jorgenson et al. ............ 607/27 |
| 6,760,624 B1* | 7/2004 | Anderson et al. ............. 607/28 |
| 2001/0031997 A1 | 10/2001 | Lee |
| 2001/0037366 A1 | 11/2001 | Webb et al. |
| 2002/0120307 A1 | 8/2002 | Jorgenson et al. ............ 607/27 |
| 2004/0122487 A1* | 6/2004 | Hatlestad et al. ............. 607/60 |

FOREIGN PATENT DOCUMENTS

| | | |
|---|---|---|
| WO | WO 02/18009 | 3/2002 |

* cited by examiner

METHOD AND APPARATUS FOR IDENTIFYING LEAD-RELATED CONDITIONS USING LEAD IMPEDANCE MEASUREMENTS

FIELD OF THE INVENTION

The present invention relates generally to implantable pulse generators, and in particular to a method for automatically identifying lead-related conditions based on lead impedance measurement trends.

BACKGROUND OF THE INVENTION

A wide variety of IMDs for delivering a therapy or monitoring a physiologic condition which may employ one or more elongated electrical leads and/or sensors have been clinically implanted or proposed for clinical implantation in patients. Such IMDs may treat or monitor the heart, muscle, nerve, brain, and stomach or other organs. IMDs such as pacemakers and implantable cardioverter defibrillators (ICDs), are available for treating cardiac arrhythmias by delivering electrical impulses to the heart. Such devices sense the heart's intrinsic rhythm through cardiac leads carrying electrodes that may be implanted in the heart. When an abnormal rhythm is detected, which may be bradycardia, tachycardia or fibrillation, an appropriate electrical therapy is delivered to restore the heart's normal rhythm.

Leads associated with such IMDs typically include a lead body extending between a proximal lead end and a distal lead end and incorporates one or more exposed electrode or sensor elements located at or near the distal lead end. One or more elongated electrical conductors extend through the lead body from a connector assembly provided at a proximal lead end for connection with an associated IMD and an electrode located at the distal lead end or along a section of the lead body. Each electrical conductor is typically electrically isolated from any other electrical conductors and is encased within an outer sheath that electrically insulates the lead conductors from body tissue and fluids.

Implantable medical leads may extend from a subcutaneous implantation site of the IMD through an internal body pathway to a desired tissue site. The leads are generally preferred having small diameter, highly flexible, reliable lead bodies that withstand degradation by body fluids and body movements that apply stress and strain to the lead body and the connections made to electrodes. As lead bodies are made smaller and smaller and the number of lead conductors is increased or maintained, problems with lead insulation and integrity of lead conductors may become more prevalent.

Cardiac lead bodies are continuously flexed by the beating of the heart. Other stresses are applied to the lead body during an implantation or lead repositioning procedure. Movements by the patient can cause the route traversed by the lead body to be constricted or otherwise altered causing stresses on the lead body. At times, the lead bodies can be slightly damaged during surgical implantation, and the slight damage may progress in the body environment until a lead conductor fractures and/or the insulation is breached. The effects of lead body damage may progress from an intermittent manifestation to a more continuous lead related condition. In extreme cases, insulation of one or more of the electrical conductors may be breached, causing the conductors to contact one another or body fluids resulting in a low impedance or short circuit. In other cases, a lead conductor may fracture and exhibit an intermittent or continuous open circuit resulting in an intermittent or continuous high impedance.

Other problems can arise at the proximal lead end where the electrical connection between IMD connector elements and the lead connector elements may be intermittently or continuously disrupted, resulting in a high impedance or open circuit. Usually, such connector open circuit problems result from insufficient tightening of the connection mechanisms, such as a set screw, at the time of implantation followed by a gradual loosening of the connection until contact becomes intermittent or open or an incomplete lead pin insertion.

Such lead problems resulting in short or open circuits may be referred to, for simplicity, as "lead related conditions." Typically, it is necessary for an attending clinician to diagnose the nature of a lead-related condition from available data, test routines, and patient symptoms. Then, it is necessary for the clinician to take corrective action, e.g., to either replace the lead, select different electrodes for sensing or pacing, or tighten the proximal connection. In severe cases, the lead-related condition may result in premature depletion of the battery energy of the IMD, requiring its replacement.

In the case of cardiac leads, the ability to sense an intrinsic heart rhythm accurately through a lead can be impaired by any of the above described lead related conditions. Complete lead breakage impedes any sensing functions, lead conductor fractures or intermittent contact can cause electrical noise that interferes with accurate sensing. Oversensing or undersensing can occur resulting in an incorrect interpretation of the heart rhythm by a pacemaker or ICD, potentially resulting in inappropriate withholding or delivery of electrical therapy. For example, oversensing may lead to the detection of tachycardia or fibrillation resulting in the inappropriate delivery of a high voltage shock therapy. Such therapy is painful to the patient and may be experienced repeatedly if a lead related condition is not diagnosed and corrected. Such inappropriate therapies deplete the ICD battery energy prematurely and could inappropriately induce ventricular fibrillation if delivered onto the T-wave.

During cardiac pacing or defibrillation, increased impedance of the stimulation path or the short circuit of lead conductors due to one of the above-described lead related conditions can reduce the effectiveness of a pacing or shocking below that sufficient to pace or defibrillate the heart. The failure of the delivered therapy can be dangerous to the patient and/or can necessitate applying further, higher energy, pacing or cardioversion/defibrillation shocks which can increase discomfort to the patient and is wasteful of battery energy.

The issue of the integrity of cardiac leads is a serious concern due to the potentially serious consequences to the patient. Certain pacemakers and ICDs have been provided with the capability of storing cardiac electrogram data prompted by the automatic determination of oversensing or undersensing of cardiac events, loss of effective pacing, out of range lead impedance measurements, etc. Such data can be telemetered to an external programmer when the physician interrogates the IMD and used by the clinician in troubleshooting any problems.

The lead impedance data and other parameter data is typically compiled and displayed on a monitor and/or printed out for analysis by the clinician. The clinician may undertake real time IPG parameter reprogramming and testing and observe the monitored surface ECG to try to pinpoint a suspected lead related condition that is indicated by the data and/or patient and/or device symptoms.

Certain external programmers that address the analysis of such data and symptoms include those disclosed in the following U.S. Pat. No. 4,825,869 (Sasmor et al.); U.S. Pat. No. 5,660,183 (Chiang et al.); and U.S. Pat. No. 5,891,179 (Er et al.), all incorporated herein by reference. The '869 patent describes processing a variety of uplink telemetered atrial and ventricular EGM data, stored parameter and event data, and the surface ECG in rule-based algorithms for determining various IPG and lead malfunctions. The '183 patent also considers patient symptoms in an interactive probability based expert system that compares data and patient systems to stored diagnostic rules relating symptoms to etiologies to develop a prognosis. The '179 patent discloses a programmer that can be operated to provide a kind of time varying display of lead impedance values in relation to upper and lower impedance limits. The lead impedance values are derived from pacing pulse current and voltage values and are either measured and stored in the IPG memory at an earlier time or comprise current, real time values that are uplink telemetered to the programmer for processing and display.

The diagnosis of lead related data at a later time in such ways is useful, but it is believed preferable to provide a more immediate response to a lead related condition by the IPG or monitor. The retrieved data may be suspect if a lead related condition causes the stored or real time telemetered data to be inaccurate. The physician may mistakenly rely upon such data to maintain or change programmed pacing parameters and modes, particularly if a lead related condition is intermittent and is not diagnosed.

Many proposals have been advanced to determine if a lead related condition has occurred and to modify the IPG operation and/or to provide a warning that is perceptible by the patient or can be telemetered to the external programmer when the physician interrogates the IPG or monitor. In addition, it has been a goal to automatically detect a lead conductor related condition and respond by switching pacing pathways to use available lead conductors that appear to be functioning properly. Prior art detection of lead related condition and various IPG responses to such detection are set forth in U.S. Pat. No. 4,140,131 (Dutcher et al.); U.S. Pat. No. 4,899,750 (Ekwall); U.S. Pat. No. 5,003,975 (Hafelfinger et al.); U.S. Pat. No. 5,137,021 (Wayne et al.); U.S. Pat. No. 5,184,614 (Collins); U.S. Pat. No. 5,201,865 (Kuehn); U.S. Pat. No. 5,224,475 (Berg et al.); U.S. Pat. No. 5,431,692 (Hansen et al.); U.S. Pat. No. 5,507,786 (Morgan et al.); U.S. Pat. No. 5,534,018 (Wahlstrand et al.); U.S. Pat. No. 5,549,646 (Katz et al.); U.S. Pat. No. 5,722,997 (Nedungadi et al.); U.S. Pat. No. 5,741,311 (McVenes et al.); U.S. Pat. No. 5,755,742 (Schuelke et al.); and U.S. Pat. No. 5,814,088 (Paul et al.). All of these patents are incorporated by reference.

Most of these patents disclose systems for periodically measuring lead impedance and comparing the impedance measurements with upper and lower impedance values or ranges and either storing the data for later retrieval, and/or changing a pacing or cardioversion/defibrillation path, and/or adjusting the delivered pacing energy, and/or alerting the patient by generating sound or stimulation warning signals. Most of the above-incorporated patents depend on the generation of an impedance reading during a period of time when the pacemaker is not providing a stimulation pulse to the heart or, alternatively, sample and hold some portion or portions of a pacing or defibrillation signal, digitize some characteristic or characteristics inherent in that signal, and have that digitized signal processed by an on-board algorithm or circuit in order to produce an impedance value for the conductor under test. The impedance value is typically compared to upper and lower impedance thresholds or impedance reference value, and employed as described above. In most cases, event data comprising the signal value and time and date are stored in memory whenever the impedance value exceeds or falls below the upper and lower impedance thresholds (i.e., the lead impedance is out of range). Certain of the above-incorporated patents, e.g. the '786 patent, also provide monitoring and storage of other parameters of IPG operation, e.g., battery voltage, for later retrieval and analysis by a clinician in an uplink telemetry session. Others of the above-incorporated patents disclose some processing of the lead impedance values within the IPG, and storage of the processed data for later retrieval and analysis by the clinician. The above-incorporated '975 patent discloses measuring unipolar and bipolar lead impedances, incrementing an error counter at least when the bipolar lead impedance value is out of range, and switching to a unipolar lead configuration, if one is available that exhibits a lead impedance value that is in the acceptable impedance range. The above-incorporated '750 patent discloses measuring output energy delivered during a pacing pulse, deriving a lead impedance value therefrom that is compared to a moving average impedance value, and incrementing a first error counter if a series, e.g., three, of such lead impedance values are out of range. In addition, characteristics of sensed heart signals are monitored, and the count of a second error counter is incremented if a series of the sensed heart signals exhibit an abnormality, e.g. an abnormal slew rate that could be due to a lead related condition. The counts are interrogated and displayed by an external programmer in an uplink telemetry session to alert the clinician of a possible lead related condition that should be investigated.

The '742 patent discloses an ICD lead impedance measurement system that measures impedance of all of the cardioversion/defibrillation leads and pacing leads using three leads at a time. A force lead and a measure lead are selected to drive current through a lead under test and to measure the voltage induced in the lead under test. Lead impedance values are derived and compared to upper and lower impedance thresholds. Out of range lead impedance value data causes an invalid flag to be set, may cause a patient warning to be emitted, and is stored as event data for later interrogation and uplink telemetry to the external programmer. The uplink-telemetered data is applied to sets of impedance rules for determining short circuit and open circuit lead related conditions. It is suggested that these rules and the testing process could be incorporated into the IPG to set a flag that identifies the lead defect and to emit a patient alert.

U.S. Pat. No. 6,317,633, issued to Jorgenson et al., incorporated herein by reference in its entirety discloses a self-testing system providing a lead status report that identifies particular lead-related condition for each lead employed in an IMD based on comparisons of periodic lead impedance measurements to upper and lower limits and loss of capture values. Optionally, such a monitor would cause a patient warning to be emitted and enable the IMD to alter its operating mode or to discontinue using a defective lead.

Comparison of a lead impedance measurement taken at a particular point in time to a fixed range of acceptable values or a fixed reference value can be useful in detecting a lead-related condition that has already manifested itself as an extremely high or extremely low impedance. Setting a fixed range, however, does not allow gradually occurring lead conditions to be detected early on. Defining a fixed range more narrowly in order to detect a lead condition earlier may result in undesired false positive detections causing a clinician to spend time investigating a problem that may not exist. A lead-related condition that is gradually worsening over time may still affect lead and IMD performance. Such conditions are preferably caught early to prevent clinical manifestation of the problem. Therefore, it is desirable to monitor trends of lead impedance changes so that a gradually occurring condition may be detected early on. Furthermore, recognition of the time course of the development of a lead-related condition may be important in diagnosing the cause and allowing prompt, appropriate corrective action. The above cited '750 patent addresses this issue in part by determining a moving average of a measured impedance and counting deviation from the norm.

Specific types of lead-related conditions may be associated with certain types of lead designs. For example, degradation of insulation between conductors may be specific to certain types of leads having coiled conductors arranged coaxially within the lead body, isolated from each other by an intervening insulating layer. After chronic exposure to the considerably hostile environment within the human body, the middle layers of insulation may break down between the conductors within the lead body. Metal ionized oxidation of the middle layers is thought to be the mechanism behind this type of middle insulation degradation which allows the infiltration of body fluids to create a short between two conductors running coaxially. The gradual degradation of the middle insulating layer results in a gradual decrease in sub-threshold impedance measured between the two electrodes associated with the two shorted conductors. This phenomenon has been observed between the ring electrode conductor and the coil electrode conductor in true bipolar cardiac defibrillation leads. Because the ring electrode is generally used for sensing the heart's intrinsic rhythm, a short between the ring electrode conductor and the coil conductor may produce oversensing and result in inappropriate therapy deliveries. Measurement of the impedance between the ring and coil electrodes show a decline, however, this decreased impedance could also be the result of an outer insulation breach.

Therefore, in some situations, a single lead-impedance measurement may not be adequate to specifically diagnose a lead-related condition. This problem is partially addressed by U.S. Pat. No. 5,944,746, issued to Kroll, incorporated herein by reference in its entirety. A system is disclosed for periodically obtaining a lead impedance measurement from a pacing tip to a high voltage shocking coil. The impedance is compared to a previously obtained measurement to determine if the impedance has increased. The system is further adapted to compare the impedance measurement to the impedance measured between the pacing lead and the casing of the implantable device to determine whether any increase in the measured impedance is due to a problem with the pacing lead or a problem with the high voltage coil or high voltage lead.

Since problems associated with lead-related conditions may be intermittent and are not routinely encountered in all patients, the task of recognizing and trouble-shooting lead-related conditions can be challenging to the physician. What is needed, therefore, is an automated method for detecting a lead-related condition based on trends in lead impedance measurements, which may include comparisons of measurements made along multiple conductive pathways. Furthermore, it is desirable that detection of lead-related conditions occurs prior to clinical manifestations that may pose risk to the patient. Reliable diagnosis of lead-related conditions will allow a physician to make prompt corrective actions with confidence and may allow an implantable device to make automated corrective actions.

SUMMARY OF THE INVENTION

The present invention addresses the problem of detecting lead-related conditions by providing a system and method for automatically monitoring trends in periodic lead impedance measurements and detecting a lead-related condition, which may be an open circuit due to a conductor fracture or poor connection to an IMD, or a short circuit due to an insulation breach. Detection of a lead-related condition is made by comparing periodic impedance measurements to relatively short-term and relatively longer-term impedance parameters. A recommended course of action to correct the problem may optionally be provided and/or a patient notification signal may be delivered.

The present invention includes an IMD capable of performing automated, periodic impedance measurements for any or all of the conductor pathways available in the lead system used with the IMD. The IMD includes a memory for storing impedance measurements made over time and preferably includes processing capabilities for determining impedance measurement parameters such as maximum, minimum and median impedance values for a given number of consecutive impedance measurements. Relatively short-term impedance parameters and relatively longer-term impedance parameters are determined for monitoring the short and long-term trends of a measured impedance. A periodic impedance measurement may be compared to impedance trend parameters, according to a set of diagnostic criteria for the detection of a lead related condition, either through onboard processing within the IPG or offline processing by an external device after uplinking impedance data from the IMD.

General diagnostics for detecting an open or short circuit may be used with a variety of lead types and may be optimized for a particular lead by setting diagnostic criteria based on known normal impedance ranges and/or abnormal impedance trends for a particular lead. Diagnostic methods may be further enhanced by including additional methods for diagnosing lead-related conditions that are characteristic of a particular lead design.

In one embodiment, a method for detecting and diagnosing middle insulation degradation due to metal ion oxidation is provided. This method includes evaluation of relatively long-term trends of multiple impedance measurements to verify middle insulation degradation and exclude other insulation problems and exclude lead types that are not subject to this type of lead-related condition.

The present invention is thus intended to relieve a clinician of the burden of detecting and evaluating a possible lead related condition. Furthermore, the present invention is intended to detect lead-related conditions with high specificity to avoid unnecessary invasive actions that put a patient at risk or time-consuming testing that inconveniences both the physician and patient. Automated diagnosis of lead-related conditions may improve the safety of an associated IMD by early detection of lead-related conditions that may manifest clinically as inappropriate withholding or delivery of electrical therapy.

DETAILED DESCRIPTION OF THE INVENTION

The present invention is aimed at providing a system and method for automatically detecting and diagnosing lead-related conditions based on impedance measurement trends. The methods included in the present invention may be used in conjunction with, or incorporated in, an implantable cardiac stimulation device such as a pacemaker or an ICD, or other devices requiring a lead for stimulating excitable tissue. Preferably, methods included in the present invention are fully implemented in an implanted device. Alternatively, methods included in the present invention for analyzing trends in lead impedance measurements that have been stored by an implantable device may be implemented in an external device capable of receiving stored impedance data through uplinking telemetry.

Figure 1:
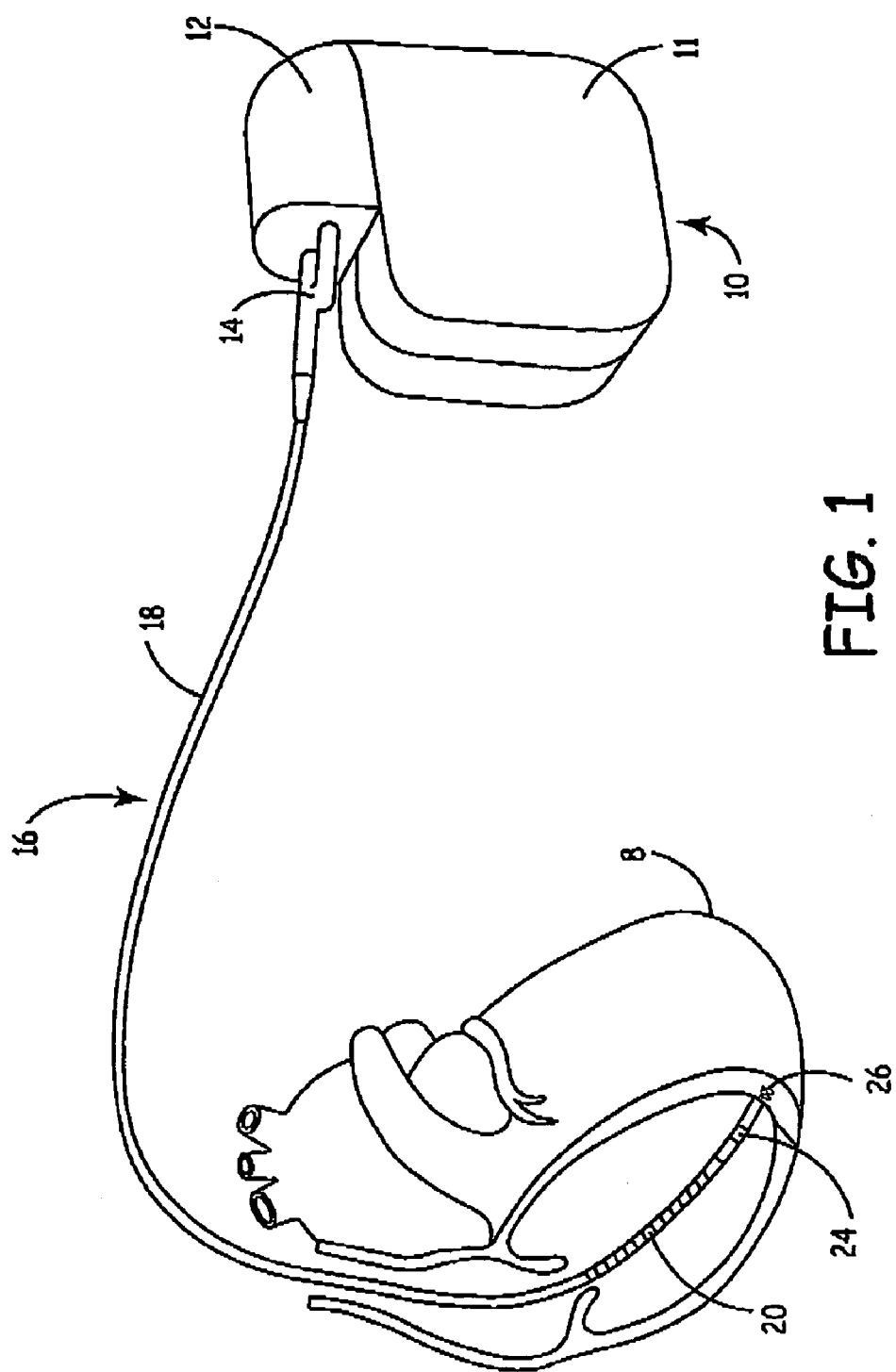
FIG. 1 is an illustration of an implantable cardiac stimulation device capable of pacemaking, cardioversion, and defibrillation in communication with a patient's heart via a stimulation and sensing lead.

An exemplary ICD 10 is shown in FIG. 1, with which methods included in the present invention may be used. The ICD 10 is shown coupled to a patient's heart by way a right ventricular lead 16. A connector block 12 receives a bifurcated connector 14 at the proximal end of lead 16 for providing electrical connection to the ICD 10. Lead 16 is positioned such that its distal end is in the right ventricle for sensing right ventricular cardiac signals and delivering pacing or shocking pulses in the right ventricle. For these purposes, lead 16 is equipped with a ring electrode 24, a tip electrode 26, and a coil electrode 20, each of which are connected to an insulated conductor within the body of lead 16. The proximal end of the insulated conductors are coupled to corresponding connectors carried by bifurcated connector 14.

Electrodes 24 and 26 may be used as a bipolar pair, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with defibrillation coil electrode 20 for defibrillation of the heart. It is recognized that alternate lead configurations may be substituted for the right ventricular lead illustrated in FIG. 1.

While a particular single-chamber ICD and lead system is illustrated in FIG. 1, it is understood that methodologies included in the present invention may be adapted for use with any single chamber device and may be expanded for use with dual chamber, or multichamber ICD or pacemaker systems including multiple leads each carrying one or more electrodes. The methodologies included in the present invention may alternatively be used in other types of electrical pulse generator systems that require implantable leads for stimulating or sensing excitable body tissue.

Figure 2:
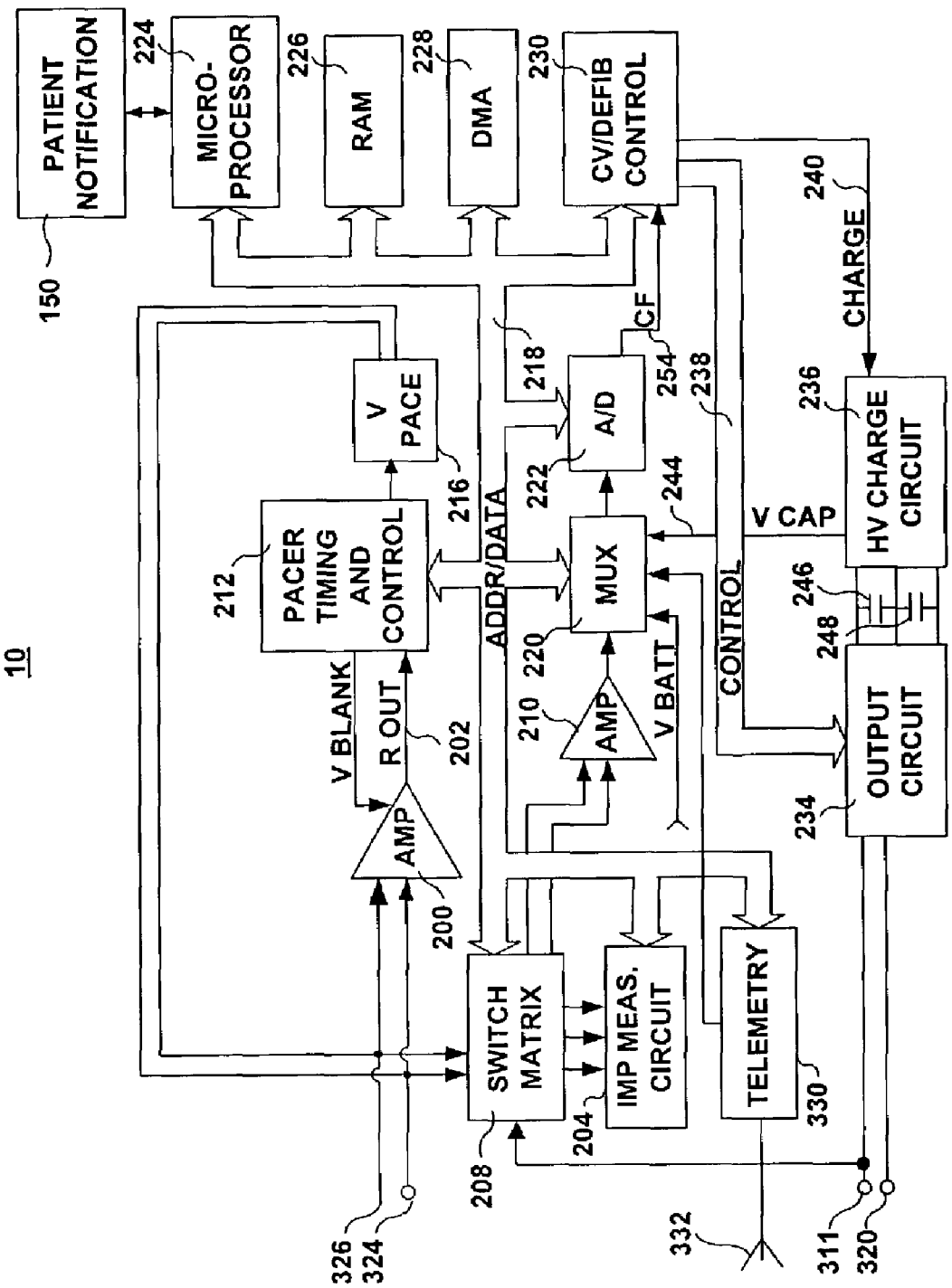
FIG. 2 is a functional, block diagram of the implantable pacemaker cardioverter defibrillator shown in FIG. 1, in which methods included in the present invention may be implemented.

A functional schematic diagram of ICD 10 of FIG. 1 is shown in FIG. 2. This diagram should be taken as exemplary of the type of device with which the invention may be embodied and not as limiting. The disclosed embodiment shown in FIG. 2 is a microprocessor-controlled device, but the methods of the present invention may also be practiced with other types of devices such as those employing dedicated digital circuitry.

With regard to the electrode system illustrated in FIG. 1, the ICD 10 is provided with a number of connection terminals for achieving electrical connection to the electrodes of lead 16. The connection terminal 311 provides electrical connection to the housing 11, also referred to herein as "can," for use as the indifferent electrode during unipolar stimulation or sensing. The connection terminal 320 provides electrical connection to defibrillation coil electrode 20 and is coupled to a high voltage output circuit 234 to facilitate the delivery of high energy shocking pulses to the heart using coil electrode 20 and housing 11.

The connection terminals 326 and 324 provide electrical connection to tip electrode 26 and the ring electrode 24 positioned in the right ventricle. The connection terminals 326 and 324 are further coupled to a ventricular sense amplifier 200 for sensing ventricular signals.

The ventricular sense amplifier 200 preferably takes the form of automatic gain controlled amplifier with adjustable sensing threshold. The general operation of the ventricular sense amplifier 200 may correspond to that disclosed in U.S. Pat. No. 5,117,824, by Keimel, et al., incorporated herein by reference in its entirety. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. Received telemetry is provided to microprocessor 224 via multiplexer 220. Numerous types of telemetry systems known in the art for use in implantable devices may be used.

ICD 10 preferably includes an impedance measurement circuit 204 for performing lead impedance measurements under the control of microprocessor 224. Impedance measurements are preferably performed on a predetermined periodic basis, which may be daily or more or less frequently. Measurements may be performed at a particular time of day, such as during the night when the patient is at rest. The frequency by which impedance measurements are made may be fixed but is preferably programmable such that if a lead-related condition is suspected, impedance measurements may be selectively performed more frequently for diagnosing the lead condition. The frequency of lead impedance measurements may alternatively be adjusted automatically based on the variation between successive measurements as generally described in U.S. Pat. No. 6,129,746 issued to Levine, et al., incorporated herein by reference in its entirety. Impedance measurements may additionally be performed following a manually entered command received by telemetry circuit 330 from an external programmer. Impedance measurements may additionally be performed upon an event trigger, such as a failed pacing pulse detected as a loss of capture. (Do measurements have to be periodic or could they also be triggered measurements that occur, for example due to loss of capture or another event?) Yes, they could be triggered, with another example being a non-physiologic RR interval of 120 ms. Automatic lead impedance measurement initiated by the occurrence of predetermined events is disclosed in the '975 patent to Hafelfinger, et al.

Depending on the type of lead and electrodes present, both high voltage and low voltage lead impedance measurements may be performed. Impedance measurement circuit 204 selects electrodes across which an impedance is to be measured via switch matrix 208. Measured impedances may be stored in a designated area of RAM 226 with a corresponding time and date label.

In the configuration shown in FIG. 1, a low voltage impedance may be measured between tip electrode 26 and ring electrode 24 to determine a pacing impedance. An exemplary pacing impedance measurement may be performed by delivering a 120 mV, 60 µs pulse applied to the tip electrode 26 60 ms after a ventricular pacing pulse or sensed R-wave and measuring the resulting current at the ring electrode 24. A high voltage impedance measurement may be performed by delivering a 400 mV, 60 µs pulse which may be applied between the coil electrode 20 and ring electrode 24, coil electrode 20 and can 11, the ring electrode 24 and can 11, and the tip electrode 24 and coil electrode 20 to evaluate various possible conduction pathways that have a changed impedance if a conductor fractures or its insulation fails.

Impedance measurements may alternatively be performed according to methods known in the art. Examples of impedance measurement techniques are disclosed in the '742, '746, '081 and '311 patents and in U.S. Pat. No. 5,897,577 issued to Cinbis et al., U.S. Pat. No. 6,242,585 issued to Prutchi et al., U.S. Pat. No. 5,215,081 issued to Ostroff, all of which patents are incorporated herein by reference in their entirety.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various pacing modes or anti-tachycardia pacing therapies. Pacer circuitry 212 also determines the amplitude of the cardiac pacing pulses under the control of microprocessor 224.

During pacing, escape interval counters within pacer timing and control circuitry 212 are reset upon sensing of R-waves as indicated by signals on line 202. In accordance with the selected mode of pacing, pacing pulses are generated by ventricular pacer output circuit 216. The pacer output circuit 216 is coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals for detecting the occurrence of a variety of arrhythmias.

The microprocessor 224 includes associated ROM in which stored programs controlling the operation of the microprocessor 224 reside. A portion of the random access memory 226 may be configured as a number of recirculating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microcontroller 224 into the pacer timing and control circuitry 212. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, ICD 10 is preferably equipped with a patient notification system 150. Any patient notification method known in the art may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Figure 3:
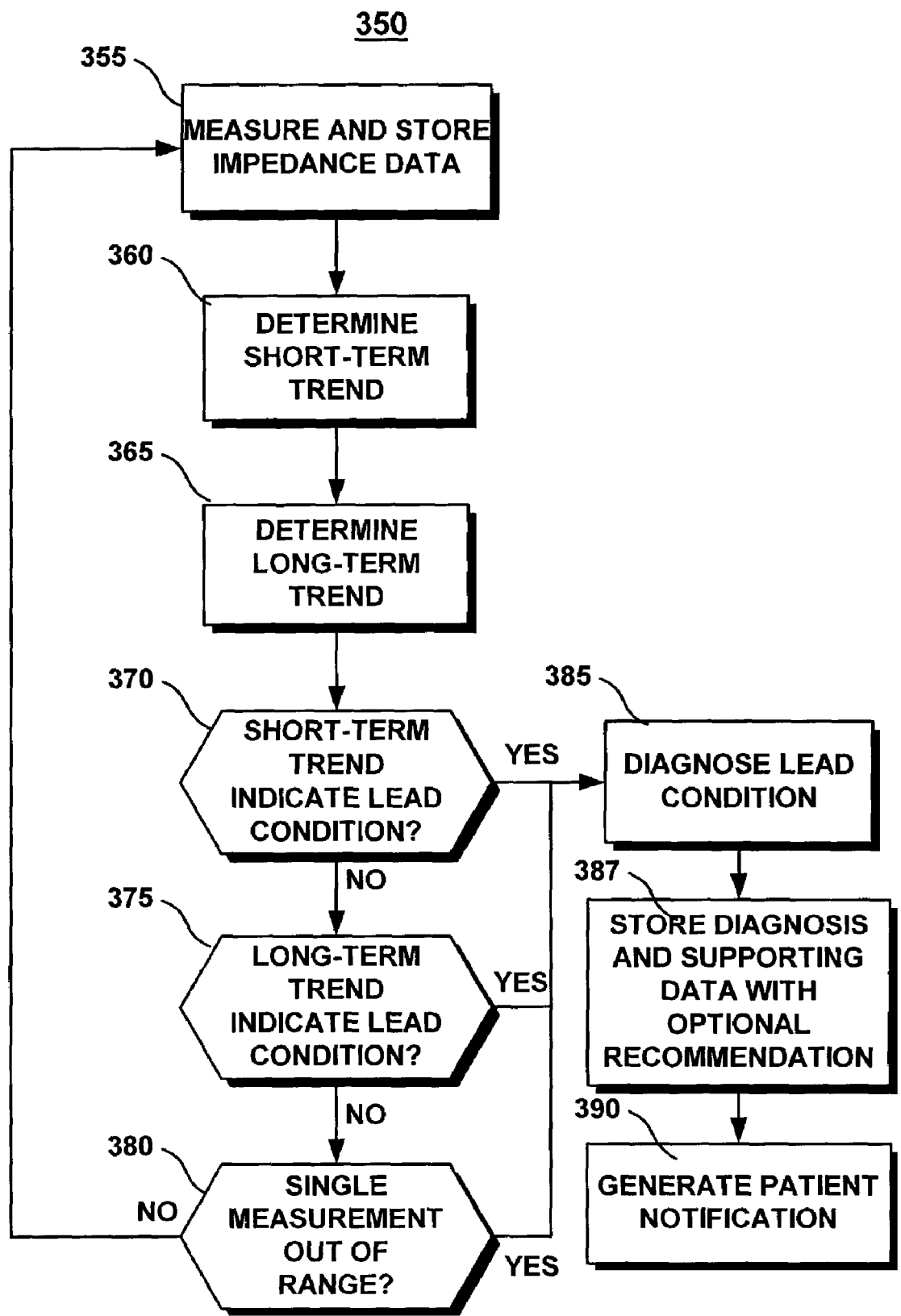
FIG. 3 is a flow diagram providing an overview of the operations included in the present invention for monitoring impedance trends for the detection and diagnosis of lead-related conditions.

FIG. 3 is a flow diagram providing an overview of operations included in the present invention for monitoring impedance trends and detecting a lead-related condition based on these trends. The method 350 requires the measurement and storage of lead impedances at step 355. Lead impedance measurements may be made on a periodic basis, preferably at least daily. Multiple periodic impedance measurements may be made depending on the number of leads present and the number of electrodes and conductors carried by each lead. For the configuration shown in FIG. 1, a preferred set of lead impedance measurements includes a low voltage pacing impedance measured across tip electrode 26 and ring electrode 24 and high voltage impedances measured across: 1) ring electrode 24 and can 11, 2) ring electrode 24 and coil electrode 20, 3) tip electrode 26 and coil electrode 20, and 4) tip electrode 26 and can 11.

Based on measured and stored lead impedances, relatively short-term impedance trend parameters are determined at step 360, and relatively long-term impedance trend parameters are determined at step 365. These short- and long-term impedance trend parameters are examined at decision step 370 and 375 to determine if the trends are indicative of a lead-related condition. This examination may include comparing a periodic impedance measurement to impedance trend parameters to determine if diagnostic criteria for detecting a lead-related condition are met. If any of the examined trends are indicative of a lead condition, the condition is diagnosed at step 385 based on the trend analysis. The diagnosed condition and supporting data may be stored in memory 226 at step 387 so that a clinician may upload this information to an external device for review. A corrective action may optionally be recommended which may be to check for a loose connection between a lead and the associated IMD or replace a lead or add an additional lead while continuing to use the functioning part of the old lead. At optional step 390, patient notification signal may be generated so that the patient is aware of a potential problem and seeks medical attention.

As a safety check in case of a sudden lead failure, a most recent lead impedance measurement may be compared to an acceptable range at decision step 380. An acceptable range may be a predefined range of impedances known to be normal for a particular lead type. If a single measurement is out of the acceptable range, a lead-related condition is diagnosed at step 385. If no trend or single impedance measurement indicate a lead-related condition as determined at decision step 370, 375 and 380, the method 350 may operate in a looping fashion by returning to step 355 to continue measuring and storing impedance data and updating the short-term and long-term impedance trends at steps 360 and 365.

Periodic impedance measurements are performed by impedance measurement circuit 204 under the control of microprocessor 224 and are stored in memory 226 of ICD 10. In one embodiment, impedance measurement data may be uplinked to an external device for analysis. Such data storage and transmission is provided in commercially available devices, for example in the GEM® Implantable Cardioverter Defibrillator available from Medtronic, Inc., Minneapolis, Minn. Determination and analysis of impedance trend parameters for detecting a lead-related condition may then be performed by an external device, which may be a programmer or personal computer. Uplinked impedance data may be alternatively be transferred via Internet to a central computer for analysis at a remote location. Reference is made to U.S. Pat. Appln. No. 20010031997 entitled "Instrumentation and software for remote monitoring and programming of implantable medical devices (IMDs)" to Lee, and U.S. Pat. Appln. No. 20010037366 entitled "System and method for providing remote expert communications and video capabilities for use during a medical procedure" to Webb et al., both patents incorporated herein by reference in their entirety. Alternatively, impedance trend parameters may be determined by programs executed by microprocessor 224 and stored in memory 226. Subsequent analysis of impedance trends may be performed by microprocessor 224 or by an external device after uplinking a history of impedance measurements and impedance trend parameters from ICD 10. Preferably, the operations shown in FIG. 3 are performed in real-time by ICD 10 such that a lead-related condition may be detected early on and patient notification signal may be generated to alert the patient to seek medical attention. The detected lead-related condition and supporting data may then be uplinked to an external device for review by a physician, who may then take prompt action to confirm and correct the problem.

The operations summarized in FIG. 3 are shown in greater detail in the flow charts of FIGS. 4 through 7. FIG. 4 is a flow diagram detailing the methods for determining short- and long-term impedance trend parameters that may be included in one embodiment of the impedance trend monitoring method 350 of FIG. 3. In a preferred embodiment, impedance measurements are made at least daily and each daily impedance measurement is stored in memory 226 at step 405. A given number of daily (or otherwise periodic) impedance measurements may be stored for a predetermined term, for example the most recent 14 daily impedance measurements may be stored as short-term impedance measurements for determining a relatively short-term impedance trend.

A relatively longer term may be defined for determining long-term impedance trends. In a preferred embodiment, a long-term is defined as one week. The maximum impedance measurement measured over the relatively longer term and the minimum impedance measurement measured over the relatively longer term are preferably determined as the long-term maximum and long-term minimum impedances. In method 400, a weekly maximum impedance is determined and stored at step 410, and a weekly minimum impedance is determined and stored at step 415.

From the stored daily (short-term) measurements and weekly (long-term) impedance parameters, short-term and long-term trends may be determined. At step 420, a short-term median impedance is determined from a predetermined number of recent, consecutive periodic measurements. In a preferred embodiment, the median of 14 daily impedance measurements is determined.

Figure 4A:
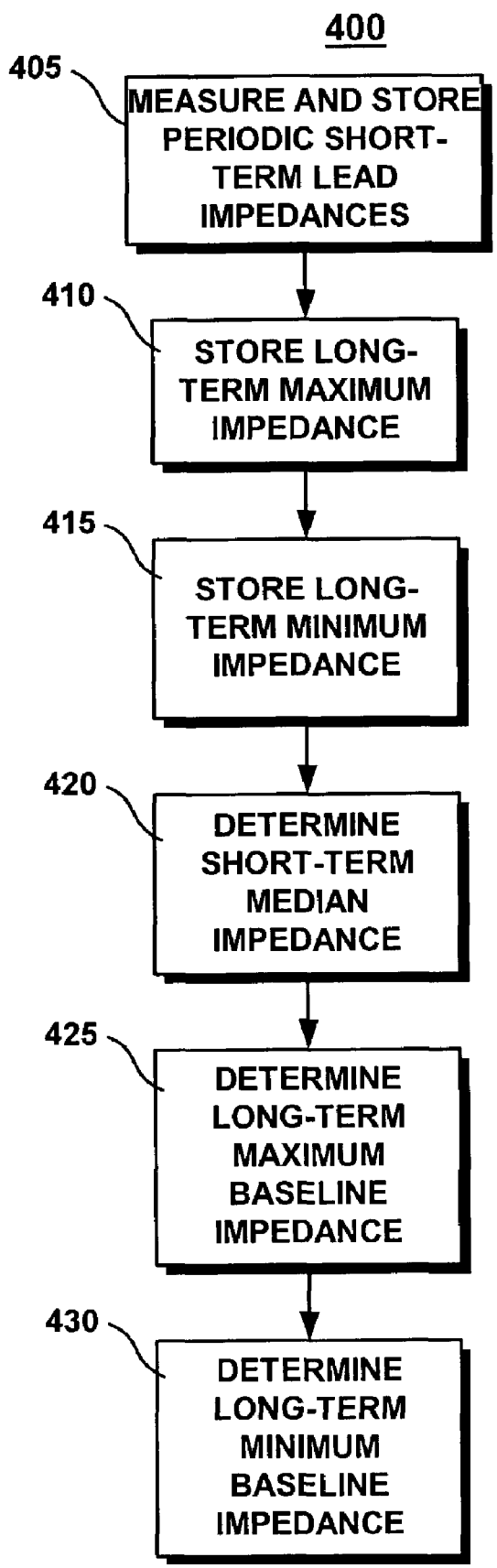
FIG. 4 is a flow diagram detailing the methods for determining short- and long-term impedance trends that may be included in one embodiment of the impedance trend monitoring method of FIG. 3.
FIG. 4B is a graph of hypothetical daily impedance data.
FIG. 4C is graphic illustration of one method for determining long-term maximum and minimum baselines.
Figure 4B:
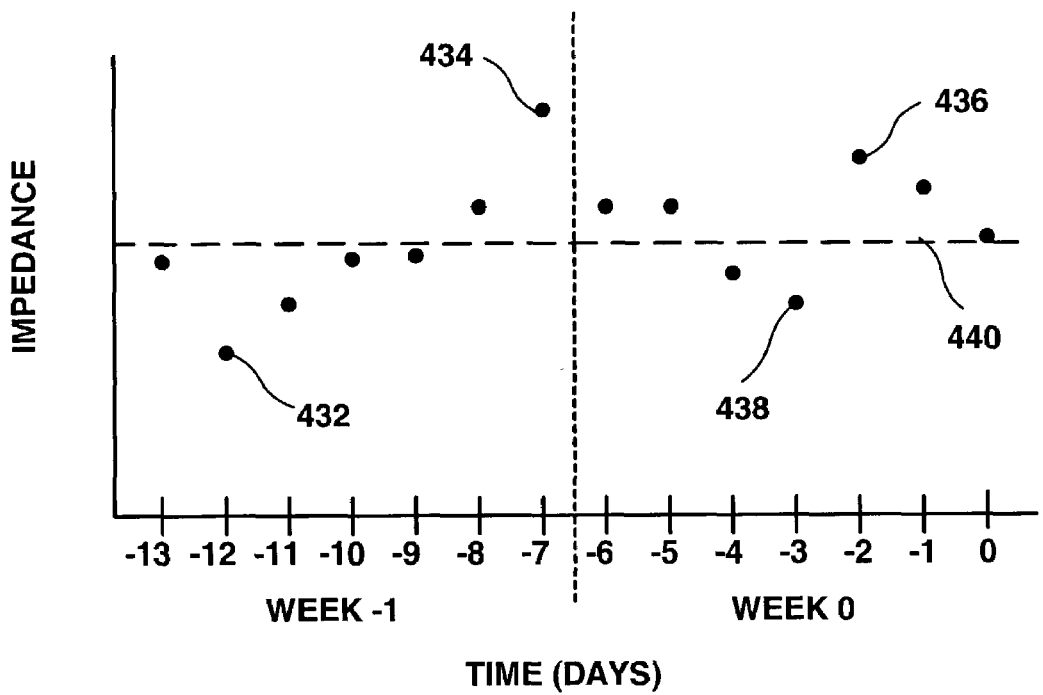

FIG. 4B is a graph of hypothetical daily impedance data. Fourteen daily impedance measurements are plotted vs. time, from day 0 through 13 days prior. The median daily impedance 440, indicated approximately by dashed line, is determined from the 14 daily impedance measurements to monitor the trend of short-term impedances. In addition, as described above, a weekly minimum impedance measurement and a weekly maximum impedance measurement is determined for each week and stored in memory 226. The highest impedance measurement 436 and the lowest impedance measurement 434 made during week 0 are stored as the weekly maximum and minimum impedance measurements for week 0. Likewise, the highest measurement 434 and lowest measurement 432 made during week −1 are stored as the weekly maximum and minimum impedances for week −1.

At step 425 of FIG. 4A, a maximum baseline is determined from stored long-term maximum impedance measurements. At step 430 a minimum baseline is determined from stored long-term minimum impedance measurements. In a preferred embodiment, trends of long-term maximum impedances and long-term minimum impedances are examined exclusively from each other. Other algorithms could be designed that combine both maximum and minimum impedances The maximum and minimum impedance measurements made over a period of time may deviate significantly from a median measurement if a short or open has occurred along an impedance measurement pathway. For example, if a conductor fracture has occurred, a high impedance may be measured. The high impedance measurement may be intermittent, however, due to motion of the lead body. Periodic impedance measurements for the same pathway, therefore, may continue to fall in a normal range, or close to a median, with an occasional or gradually increasing maximum impedance. A trend of increasing long-term maximum impedance may therefore occur with a relatively stable minimum long-term impedance.

In another example, if a conductor insulation is breached, a low impedance measurement may occur. Again, a low impedance measurement may be intermittent due to lead movement resulting in some periodic impedance measurements to be relatively normal. A trend of decreasing long-term minimum impedance may occur with stable long-term maximum impedance. Thus, the trends in the weekly maximum and minimum impedances may be different and mutually exclusive, depending on the type of lead-related condition that may be present. In accordance with the present invention, therefore, a maximum weekly baseline and a minimum weekly baseline are determined to allow mutually exclusive analysis of trends in these parameters.

Figure 4C:
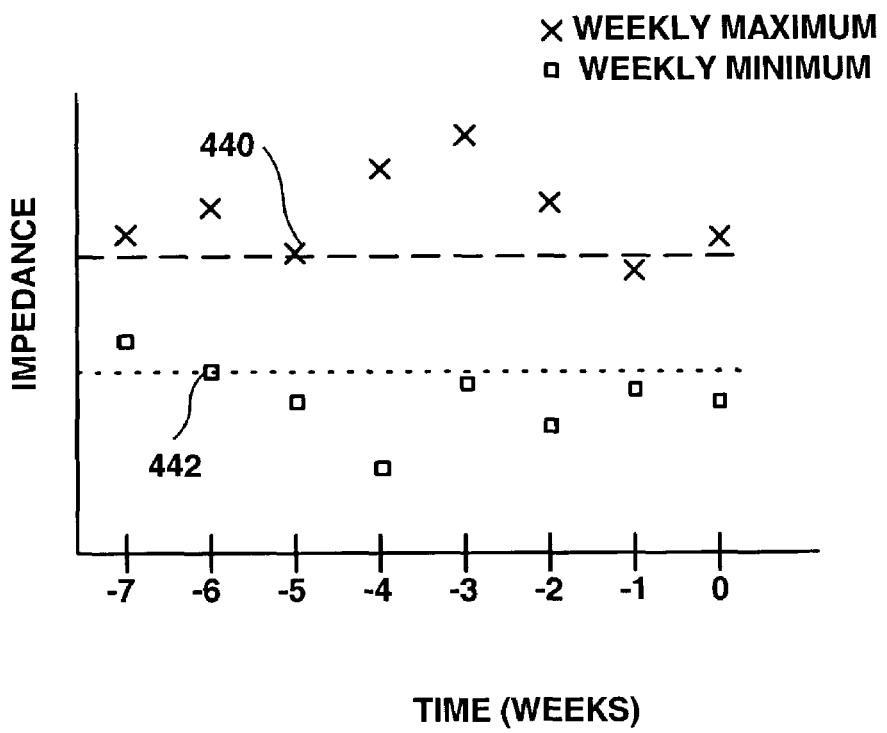

A long-term maximum and minimum baseline may be determined based on the long-term maximum and minimum impedance measurements over a given number of terms. FIG. 4C is graphic illustration of one method for determining long-term maximum and minimum baselines. In FIG. 4C, 8 weeks of maximum and minimum weekly impedance values are plotted vs. time, from week 0 through 7 weeks prior. A long-term maximum baseline 440 is determined as the second lowest (change FIG. 4C accordingly) weekly maximum impedance determined from 8 weekly maximum impedance measurements. A long-term minimum baseline 442 is determined as the second highest weekly minimum impedance determined from 8 weekly minimum impedance measurements. By using the second lowest and second highest maximum or minimum impedance measurement for setting a maximum or minimum baseline, respectively, outliers may be ignored. Long-term maximum and minimum baseline impedances may alternatively be determined based on a median value of the maximum or minimum measurements, respectively, a percentage of a median value, or other function of the long-term maximum and minimum impedances.

Figure 5:
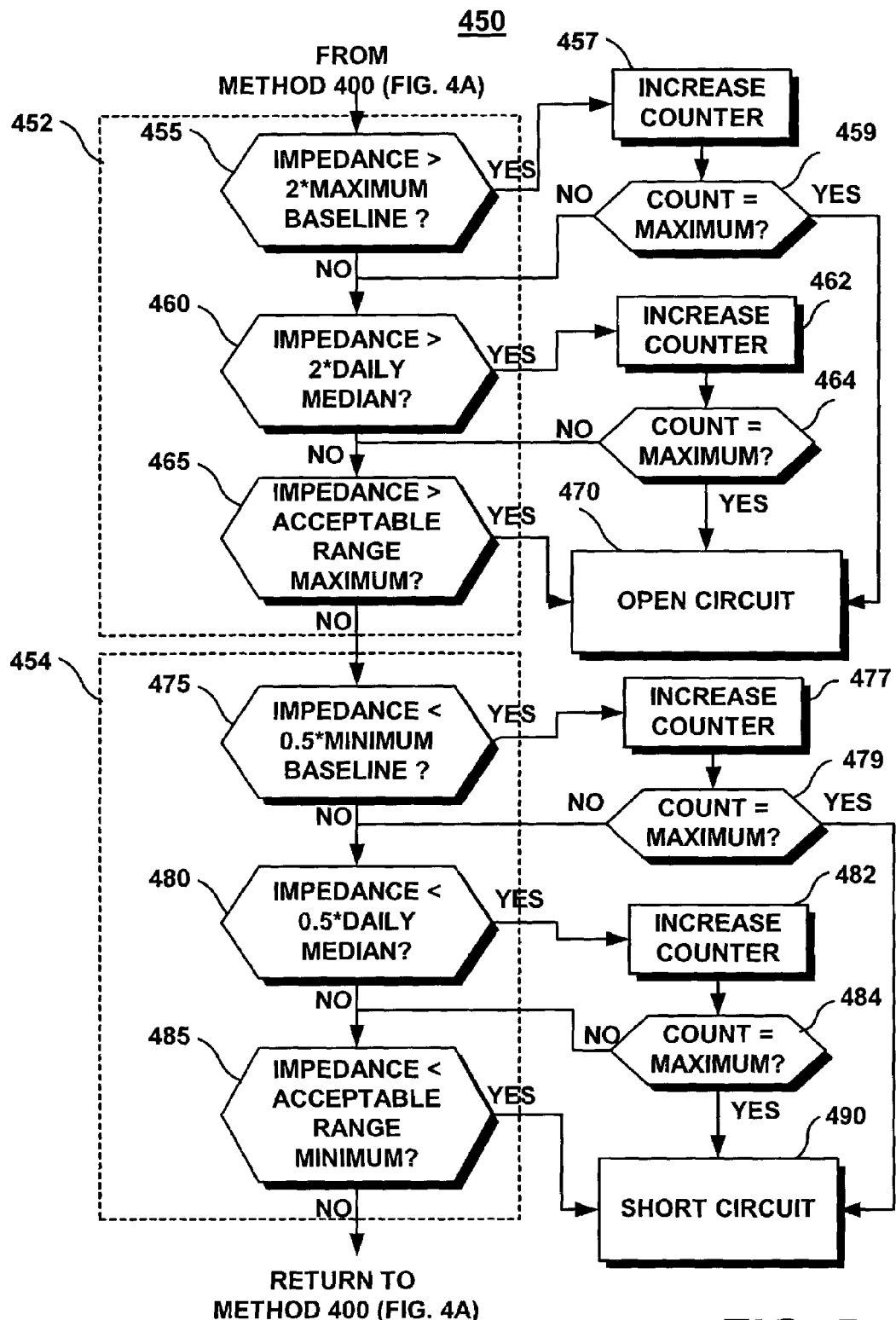
FIG. 5 is a flow chart illustrating one method that may be used by the lead impedance monitoring method of FIG. 3 for detecting an open or short circuit.

Other impedance trend parameters may be alternatively or additionally be determined such as impedance variability, slopes of short-term or long-term impedance measurements versus time, etc. Once parameters representing the short-term and long-term impedance trends have been obtained, periodic impedance measurements may be compared to the trend parameters to determine if a lead-related condition is present. Thus, method 400 of FIG. 4 may continue to method 450 of FIG. 5. FIG. 5 is a flow chart illustrating one method that may be used by the lead impedance monitoring method 350 of FIG. 3 for detecting an open or short circuit.

The decision steps 455, 460 and 465 are included in an analysis 452 for determining if an open circuit is indicated. At step 455, a periodic impedance measurement is compared to a long-term maximum baseline measurement. In the preferred embodiment, a weekly maximum impedance measurement is compared to a weekly maximum baseline determined according to the method 400 described above. The daily measurements are compared to the daily median and the weekly measurements are compared to the weekly baselines. If the weekly maximum impedance measurement is significantly greater than the weekly maximum baseline, for example 2 times greater, a counter that has been previously initialized to 0 (not shown) is increased by one count at step 457. If the counter reaches a predetermined maximum as determined at decision step 459, an open circuit is detected at step 470. In one embodiment, an open circuit is detected if three weekly maximum impedance measurements exceed twice the weekly maximum baseline.

If the periodic impedance measurement does not significantly exceed the long-term maximum baseline, the measurement is compared to the short-term median impedance at decision step 460. In the preferred embodiment, a daily impedance measurement is compared to the median of the 14 most recent daily measurements. If the measurement is significantly greater than the short-term median, for example more than twice the short-term median, a counter that has been previously initialized to 0 (not shown) is increased by one at step 462. If the counter reaches a maximum, as determined at decision step 464, an open circuit is detected at step 470. In one embodiment, an open circuit is detected if three periodic impedance measurements exceed twice the short-term median impedance.

If the periodic measurement does not significantly exceed the short-term median impedance, the periodic measurement is compared to a maximum acceptable impedance, at step 475, which may be a fixed, predetermined value or a programmable value selected based on the type of lead used. In one embodiment, an open circuit is detected at step 470 if the daily pacing impedance measurement exceeds 2000 ohms.

Thus an open circuit may be detected based on a single impedance measurement outside of a predetermined range, or, in accordance with the present invention, based on a short-term or long-term impedance trend. Diagnostic criteria set for detecting a lead-related condition based on comparisons between a periodic impedance measurement and short-term and long-term impedance parameters may be tailored to a particular lead type. For example, the difference between a periodic lead measurement and an impedance parameter trend and the number of periodic measurements deviating significantly from an impedance parameter trend may be uniquely defined depending on the type of lead being monitored. Upon detection of an open circuit, the method 350 or FIG. 3 will store the lead-related condition along with the supporting data that led to the detection (step 385) and may provide a recommended corrective action or generate a patient notification signal.

If an open circuit is not detected, the method 450 proceeds to step 475 to begin an analysis 454 for detecting a short circuit, which includes the decision steps 475, 480 and 485. At step 475, a periodic impedance measurement is compared to a long-term minimum baseline measurement. In the preferred embodiment, a weekly minimum impedance measurement is compared to a weekly minimum baseline determined according to the method 400 described above. If the weekly minimum impedance measurement is significantly less than the weekly minimum baseline, for example less than half the weekly minimum baseline, a counter, that has been previously initialized to 0 (not shown) is increased by one count at step 477. If the counter reaches a predetermined maximum as determined at decision step 479, a short circuit is detected at step 490. In one embodiment, a short circuit is detected if three daily impedance measurements are less than half the weekly minimum baseline.

If the periodic impedance measurement is not significantly less than the long-term minimum baseline, the measurement is compared to the short-term median impedance at decision step 480. In the preferred embodiment, a daily impedance measurement is compared to the median of the 14 most recent daily measurements. If the measurement is significantly less than the short-term median, for example less than half the short-term median, a counter that has been previously initialized to 0 (not shown) is increased by one at step 482. If the counter reaches a maximum, as determined at decision step 484, a short circuit is detected at step 490. In one embodiment, a short circuit is detected if three daily impedance measurements are less than half the short-term median impedance.

If the periodic measurement is not significantly less than the short-term median impedance, the periodic measurement is compared to a minimum acceptable impedance, which may be a fixed, predetermined value or a programmable value, at step 485. In one embodiment, if the daily pacing impedance measurement is less than 200 ohms, an open circuit is detected at step 470. Upon detection of a short circuit, method 350 of FIG. 3 will store the diagnosis and supporting data (step 385) in memory 226 an optionally provide a recommended corrective action or generate a patient notification signal.

If an open or short circuit is not detected by method 450 of FIG. 5, the method 450 may return to step 400 of FIG. 4A to collect the next periodic impedance measurement, update the trend parameters accordingly, and continue to test for a lead-related condition in a looping fashion. Tests for a lead-related condition may further include a more rigorous analysis of long-term trends to detect a gradually occurring condition.

FIG. 6 is a flow chart illustrating one method that may be included in impedance monitoring method 350 of FIG. 3 for detecting insulation degradation. A gradual degradation of the outer insulation of a lead body may be detected by monitoring impedance trends over a relatively long-term. Method 500 begins at step 505 by determining the running median of a given number of consecutive long-term minimum impedance measurements. In one embodiment, the median is determined from 5 weekly minimum impedance measurements. The running long-term median is then determined for a given number of terms. For example, a five-week median may be determined for 12 weeks. Next, parametric linear regression is performed on the 12 five-week median values at step 510. The slope of the linear regression, which may be a least squares fit, is then compared to a minimum acceptable slope at decision step 515. If a negative slope is found that represents a decrease in the impedance over the 12-week period of greater than a predetermined percentage, X, for example 30%, then a lead degradation problem is suspected. If the comparison made at decision step 515 is not affirmed, the method 500 returns to step 505 to continue determining a running median of the weekly minimum impedance and performing the linear regression analysis at step 510.

If the comparison at step 515 is affirmed, then a decline in impedance due to a lead replacement must be excluded before concluding that lead degradation condition exists. A single step-wise decrease in lead impedance can occur when a lead has been replaced. Therefore, to verify that the overall decrease is not due to a step-wise decrease associated with a lead replacement, the difference between each of the consecutive five-week median values used in the parametric analysis is determined at step 517. If two consecutive medians differ by greater than a predetermined amount, for example greater than 35%, as determined at decision step 520, then a lead replacement has occurred as concluded at step 530. If consecutive median differences do not indicate a step-wise change, then the gradual decrease in the running median impedance is concluded to be due to insulation degradation at step 525. This diagnosis and the supporting data are stored in memory 226 at step 385 of method 350 (FIG. 3) for later uplinking to an external device for physician review, and a recommended action and/or a patient notification signal may be generated as described previously.

Figure 6A:
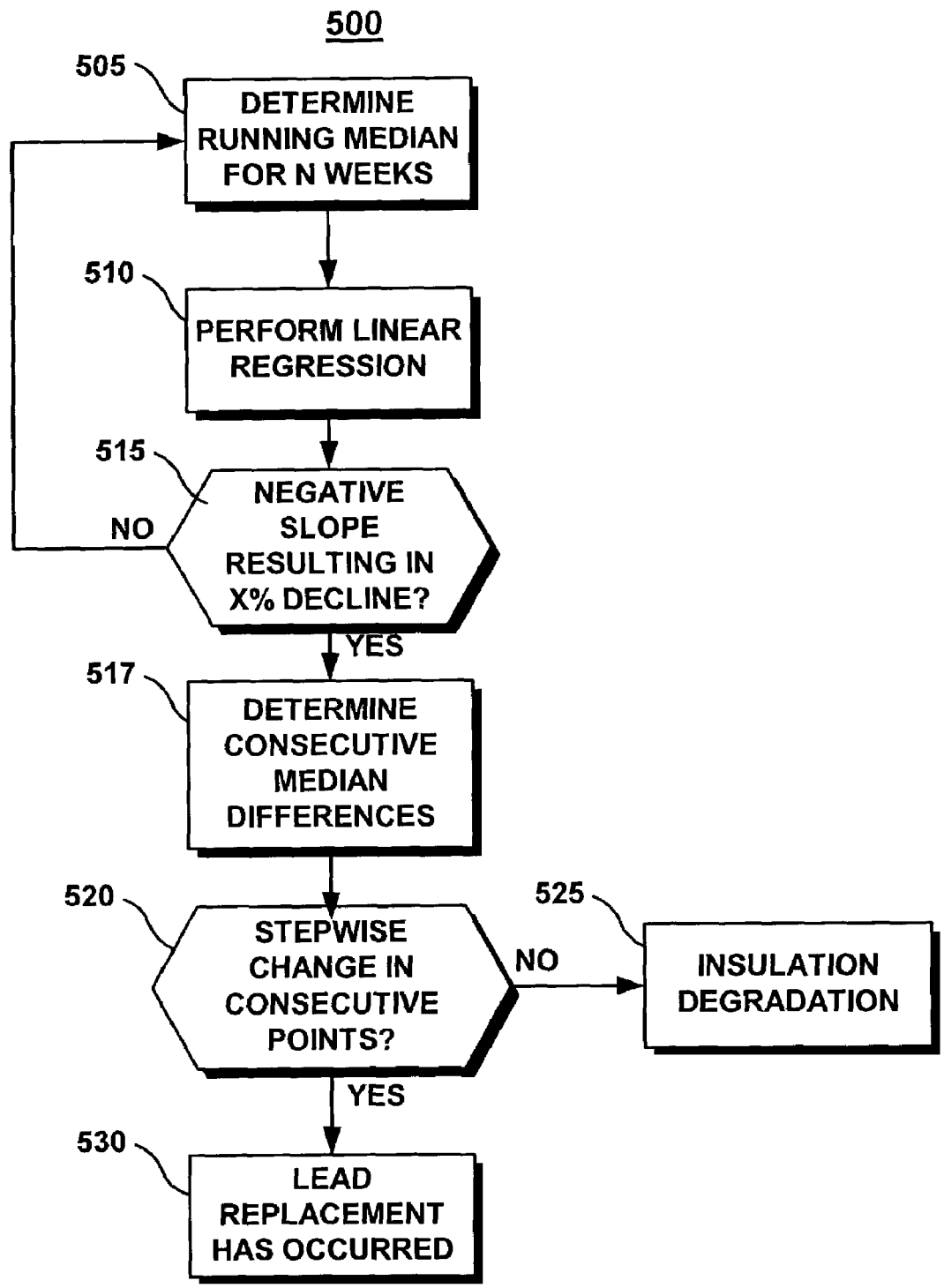
FIG. 6 is a flow chart illustrating one method that may be included in impedance monitoring method 350 of FIG. 3 for detecting insulation degradation.
FIG. 6B is flow chart summarizing an alternative method for detecting lead insulation degradation using non-parameteric methods.
Figure 6B:
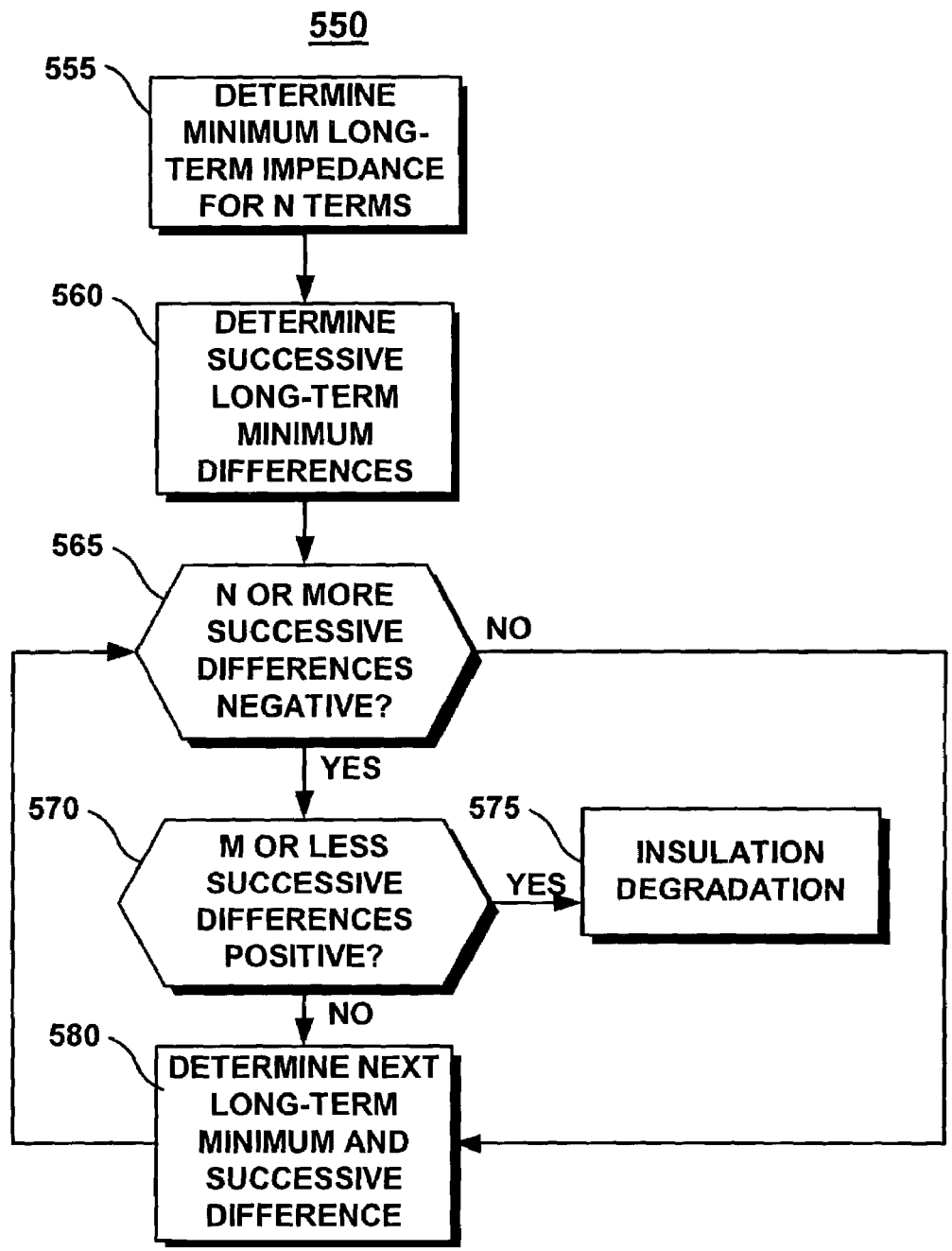

FIG. 6B is flow chart summarizing an alternative method for detecting lead insulation degradation using non-parameteric methods. In method 550, the long-term minimum impedance measurement is determined for a desired number of terms at step 555. In a preferred embodiment, a weekly minimum impedance is determined for 12 weeks. At step 560, the successive differences between the long-term minimum impedances are determined. At decision steps 565 and 570, a non-parameteric analysis is performed to determine if the successive differences indicate a gradually decreasing trend of the long-term minimum impedance. In one embodiment, a given number, N, successive differences must be negative with no more than a given number, M, successive differences being positive wherein N should be greater than M. In one embodiment, if successive differences between 12 weekly minimum impedance measurements have been determined, at least five successive differences must be negative, as determined at decision step 565, and no more than two successive differences may be positive, as determined at step 570, in order to diagnose a lead insulation degradation condition at step 575. If the diagnostic requirements of the non-parameteric analysis are not met at decision step 565 and 570, the next long-term minimum impedance and associated successive difference is determined at step 580. Method 550 may then return to step 565 to continue monitoring the successive differences to determine if the diagnostic requirements are met.

The method 450 of FIG. 5A for detecting an open or short circuit and methods 500 or 550 of FIGS. 6A and 6B for detecting insulation degradation represent general methods that may generally be applied to many lead types. Supplementary analyses of impedance trends may be performed for detecting lead-related conditions that are characteristic of a particular lead type.

One lead related condition that can occur with certain types of leads is degradation of a middle insulation layer due to metal ion oxidation. This type of degradation is observed in leads having coaxially arranged conductors separated by polyurethane insulation. This phenomenon is not observed in other types of leads, such as leads having conductors arranged in a multi-lumen, silicone rubber lead body. Therefore, supplementary analysis of impedance trend data may include an analysis for detecting and diagnosing metal ion oxidation induced degradation. In a preferred embodiment, the type of lead in which lead impedance measurements are being made is preferably known so that appropriate supplementary analyses may be made. The lead type may be entered manually as a lead model number upon implantation by the physician. If the lead type is not known, supplementary analyses preferably include tests that will exclude types of leads that would not be subject to the particular type of lead-related condition being investigated.

Figure 7:
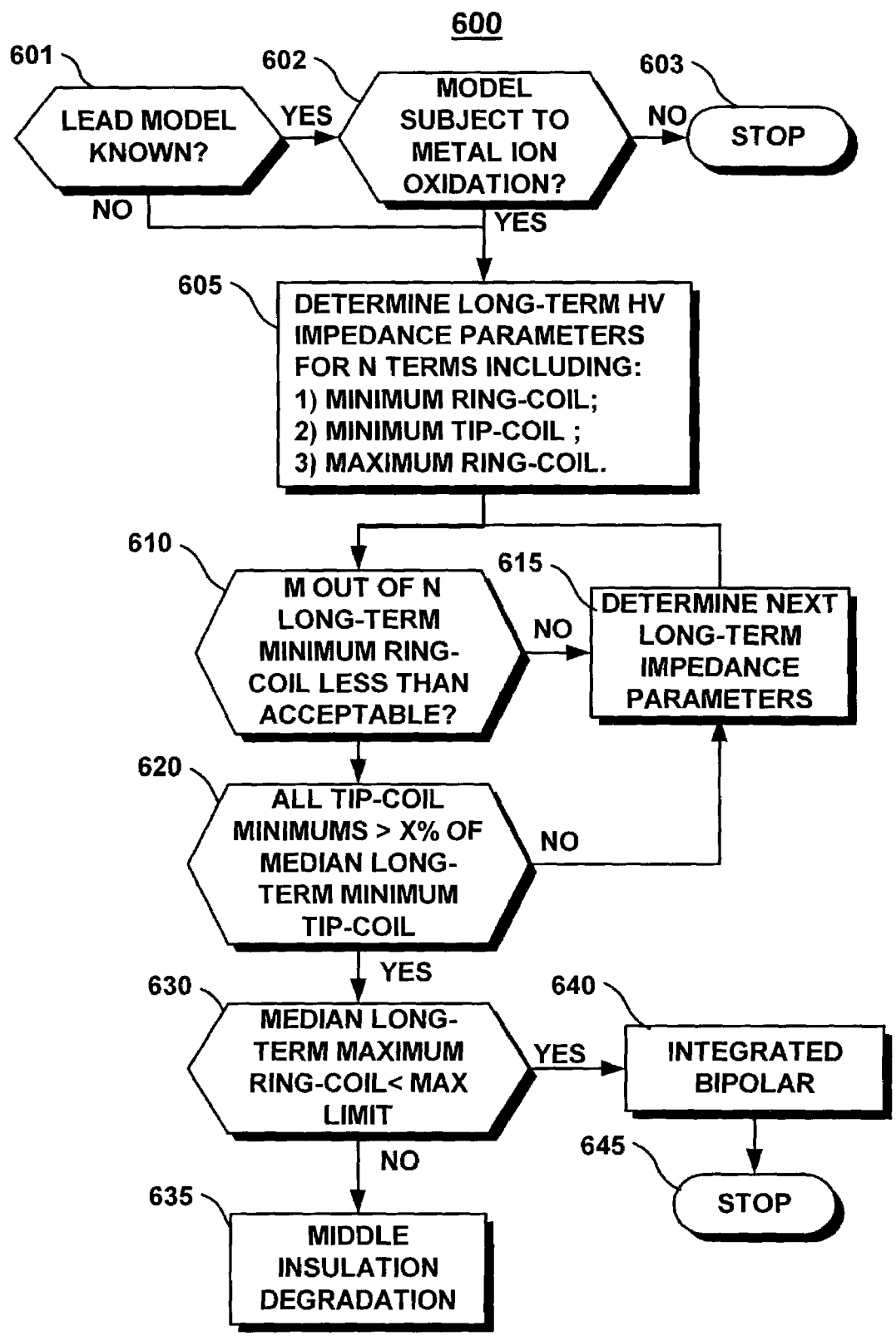
FIG. 7 is a flow chart summarizing one method for monitoring trends in lead impedance parameters for detecting middle insulation degradation due to metal ion oxidation.

FIG. 7 is a flow chart summarizing one method for monitoring trends in lead impedance parameters for detecting middle insulation degradation due to metal ion oxidation. Because this type of lead-related condition is specific to certain lead designs, method 600 begins at decision step 601 to determine if the lead model in which lead impedance measurements are being made is known. If the lead model is not known, the method 600 may continue with the analyses but preferably includes steps for excluding leads not subject to metal ion oxidation (MIO) as will be described below.

If the lead model is known, method 600 determines if the model is subject to MIO at decision step 602. The known lead model number may be compared to a list of lead model numbers known to be subject to MIO. If the lead model is not subject to MIO, method 600 is terminated at step 603. If the lead is subject to MIO, method 600 continues to step 605 to begin analyzing impedance trends.

In order to specifically diagnose middle insulation degradation, the trend of multiple lead impedance parameters is monitored. At step 605 long-term impedance parameters are determined for multiple impedance measurement pathways. Middle insulation degradation due to MIO is typically observed in true bipolar defibrillation leads having polyurethane insulation between a coil electrode and a ring electrode. When this insulation layer begins to degrade, the impedance pathway along any pathway that includes the ring electrode and/or the coil electrode is affected. At step 605, multiple long-term high-voltage (HV) impedance parameters are determined for a predetermined number of terms, N. The parameters preferably include a long-term minimum across ring and coil electrodes, a long-term minimum across the coil and can electrodes, and a long-term maximum across the ring and coil electrodes. In a preferred embodiment, the long term is a term of one week, and weekly parameters are collected for seven weeks.

At decision steps 610, 620 and 630, three criteria for diagnosing middle insulation degradation due to MIO are tested. The first criterion, tested at decision step 610, is that a given number M, of the N long-term minimum ring-to-coil impedances must be less than an acceptable level, which would indicate a short between the ring and coil electrodes due to degradation of the intervening insulation. In a preferred embodiment, any four out of seven consecutive weekly minimum ring-to coil impedances must be lower than 14 ohms. If this criterion is not met, method 600 continues to step 615 to determine the next long-term impedance parameters which will be stored in a rolling memory buffer designated for storing the most recent N parameters. After storing the new weekly parameters, the tests for MIO are repeated.

If the first criterion at decision step 610 is satisfied, the second criterion is tested at decision step 620. The second criterion is that each long-term minimum coil-can impedance is greater than a predetermined percentage of the median minimum coil-can impedance determined from the N terms. In a preferred embodiment, each weekly minimum coil-can impedance must be greater than 50% of the median of seven consecutive weekly minimum coil-can impedances. If any of the weekly minimum coil-can impedances is less than half of the median minimum coil-can impedance, then a short of the outer coil insulation may be present. An outer insulation problem will be detected and diagnosed by the methods described previously for detecting a short or general insulation degradation. When the second criterion is not met, the method 610 proceeds to step 615 to determine the next long-term impedance parameters and will continue to monitor the impedance parameters according to the MIO diagnostic criteria.

If the second criterion is met, thereby ruling out that the decrease in the ring-coil minimum impedances found at decision step 610 is not due to an outer insulation breach of the coil electrode, middle insulation degradation to MIO is likely to be present. The final criterion, tested at decision step 630, is included in the case that the lead model number is not known. If the lead model number is not known, the lead in which impedances are being measured may be an integrated bipolar lead rather than a true bipolar lead. Middle insulation degradation due to MIO has not been observed in an integrated bipolar lead. Therefore, the third criterion is provided to establish that the lead is not an integrated bipolar lead.

The ring-coil impedances measured in an integrated bipolar lead will be considerably lower than the ring-coil impedances measured in a true bipolar lead. Therefore one way to discriminate between an integrated and true bipolar lead is to monitor the maximum long-term ring-coil impedance. If this maximum remains in a lower range, typical of an integrated bipolar lead, then the lead is known to be an integrated bipolar lead, generally not subject to MIO, rather than a true bipolar lead. Conversely, if the maximum long-term ring-coil impedance remains in a higher range, associated with a true bipolar lead, then the lead is known to be a true bipolar lead that is subject to MIO.

At decision step 630, a median of a desired number of maximum long-term ring-coil impedances is compared to a predetermined maximum limit that is considered an upper boundary for the maximum ring-coil impedance of an integrated bipolar lead. In a preferred embodiment, the median of seven weekly maximum ring-coil impedances must be less than 5 ohms if the lead is an integrated bipolar lead. If this comparison is true, the lead is known to be an integrated bipolar lead as indicated at step 640. No middle insulation condition is diagnosed.

If the comparison at decision step 630 is not true, then the final criterion for diagnosing middle insulation degradation due to MIO in a true bipolar lead is satisfied as indicated at step 635. This diagnosis and supporting data may be stored in memory 225 and a recommended corrective action, which would generally be lead replacement, may be indicated. A patient notification signal may be generated.

Thus, a lead-specific condition, such as middle insulation degradation due to MIO, may be diagnosed by monitoring multiple lead impedance measurement trends. This supplementary monitoring of impedance trends may be performed in addition to monitoring one or more individual lead impedance measurement trends for diagnosing general lead-related conditions associated with sudden or gradually occurring short or open circuits. The detailed descriptions of the preferred embodiments provided herein yield a sensitive and specific method for diagnosing lead-related conditions based on short-term and long-term impedance trends. It will be apparent to those skilled in the art that numerous variations of the described embodiments are possible for practicing the invention. Therefore, the embodiments described herein should be considered exemplary, rather than limiting, with regard to the following claims.

What is claimed is:

1. A method for detecting a lead-related condition comprising:
   periodically measuring a lead impedance,
   determining a short-term impedance trend,
   determining a long-term impedance trend,
   applying a set of diagnostic criteria to the short-term and long-term impedance trends, and
   diagnosing a lead-related condition based on said set of diagnostic criteria.

2. The method of claim 1 wherein the method of periodically measuring a lead impedance includes comparing if a single measurement falls out of range.

3. The method of claim 2 wherein the method of diagnosing a lead-related condition includes subsequently storing diagnosis and supporting data with optimal recommendation and generating patient notification.

* * * * *